US009840722B2

(12) United States Patent
Dupre et al.

(10) Patent No.: US 9,840,722 B2
(45) Date of Patent: Dec. 12, 2017

(54) METHOD FOR PRODUCING HYDROCARBIDES

(71) Applicant: BIO-THINK, Chilleurs aux Bois (FR)

(72) Inventors: Jean-Yves Dupre, Vincennes (FR); Oswaldo Yaguez Rodriguez, Smarves (FR)

(73) Assignee: BIO-THINK, Chilleurs aux Bois (FR)

( * ) Notice: Subject to any disclaimer, the term of this patent is extended or adjusted under 35 U.S.C. 154(b) by 52 days.

(21) Appl. No.: 14/785,390

(22) PCT Filed: Apr. 16, 2014

(86) PCT No.: PCT/FR2014/050923
§ 371 (c)(1),
(2) Date: Oct. 19, 2015

(87) PCT Pub. No.: WO2014/170603
PCT Pub. Date: Oct. 23, 2014

(65) Prior Publication Data
US 2016/0068866 A1   Mar. 10, 2016

(30) Foreign Application Priority Data
Apr. 19, 2013 (FR) .................................... 13 53567

(51) Int. Cl.
C12P 5/02 (2006.01)
C12P 7/40 (2006.01)
C12P 7/64 (2006.01)
C25B 3/10 (2006.01)
C25B 15/08 (2006.01)

(52) U.S. Cl.
CPC ............... *C12P 5/02* (2013.01); *C12P 7/40* (2013.01); *C12P 7/6409* (2013.01); *C25B 3/10* (2013.01); *C25B 15/08* (2013.01); *Y02E 50/343* (2013.01)

(58) Field of Classification Search
CPC .. C12P 5/02; C12P 7/40; C12P 7/6409; C25B 15/08; C25B 3/10; Y02E 50/343
See application file for complete search history.

(56) References Cited

U.S. PATENT DOCUMENTS 3,992,268 A    11/1976   Antos
2011/0111475 A1   5/2011   Kuhry et al.

FOREIGN PATENT DOCUMENTS

FR    2303854       10/1976
WO    2007-095215   8/2007
WO    2011-011537   1/2011

OTHER PUBLICATIONS

Mostafa "Productin and recovery of volatile fatty acids from fermentation broth" 1999, Energy Conservation & Management, vol. 40:1543-1553.*
FR search report, dated Jan. 10, 2014; Application No. 1353567.
International search report, dated Sep. 30, 2014; Application No. PCT/FR2014/050923.
Agler et al., "Chain elongation with reactor microbiomes: upgrading dilute ethanol to medium-chain carboxylates," Energy & Environmental Science, 2012, vol. 5, pp. 8189-8192.
Choi et al., "In Situ Biphasic Extractive Fermentation for Hexanoic Acid Production from Sucrose by Megasphaera elsdenii NCIMB 702410," Appl. Biochem. Biotechnol 2013, vol. 171, pp. 1094-1107.
Kim et al., "Production of C4-C6 for Bioenergy and Biomaterials," Appl. Chem.Eng., vol. 22, No. 5, Oct. 2011, pp. 447-452.
Levy et al., "Liquid Fuels Production from Biomass," Department of Energy (DOE), Technical reports, Jan. 1, 1980, pp. 01-03.
Levy et al., "Biorefining of biomass to liquid fuels and organic chemicals," Enzyme and Microbial Technology, vol. 3, No. 3, Jul. 1, 1981, pp. 207-215.
Levy et al., "Kolbe Electrolysis of Mixtures of Aliphatic Organic Acids," Journal of the Electrochemical Society, vol. 131, No. 4, Apr. 1, 1984, pp. 773-777.
Roddick et al., "Production of Hexanoic Acid by Free and Immobilised Cells of Megasphaera elsdenii: Influence of in-situ Product Removal Using Iron Exchange Resin," J. Chem. Tech. Biotechnol. 1997, 69, pp. 383-391.

* cited by examiner

*Primary Examiner* — Robert Yamasaki
*Assistant Examiner* — Teresa E Knight
(74) *Attorney, Agent, or Firm* — Young & Thompson

(57) ABSTRACT

A method for producing hydrocarbons, includes at least the following steps: a) anaerobic fermentation of a fermentable raw material in order to produce volatile fatty acids, b) elongation of the volatile fatty acids produced in step a) by fermentation with at least one bacterium of the *Megasphaera* genus, extraction of the fatty acids produced from the fermentation broth, and c) production of hydrocarbons by subjecting the fatty acids produced in step b) to a Kolbe electrolysis.

21 Claims, No Drawings

METHOD FOR PRODUCING HYDROCARBIDES

BACKGROUND OF THE INVENTION

Field of the Invention

This invention relates to a process for the production of hydrocarbons from various biomasses. The hydrocarbons that are obtained are in particular intended to be used as automotive biofuels or heating biofuels.

Description of the Related Art

For several years, numerous countries have sought solutions for replacing petroleum, which is becoming more and more scarce and has numerous drawbacks of an economic and ecological nature.

So-called first-generation biofuels have been proposed in a first stage, but the latter are very criticized today because they enter into direct competition with food and their performance levels for combating the greenhouse effect are contested because of the release of $CO_2$ linked to the indirect change of soil assignment for continuing to feed the world population.

The use of biomethane produced from anaerobic fermentation has also been developed, but it requires the installation of very costly distribution systems and vehicles that are specifically equipped for operating with natural gas.

Other biofuels start from sugars or fatty substances from which oxygen is eliminated to obtain hydrocarbons, by hydrogenation processes that are costly because they require large quantities of hydrogen.

SUMMARY OF THE INVENTION

The objective of this invention is to propose a solution that remedies these drawbacks, owing to products that are usable in all existing motors and that enter into the category of second- and third-generation biofuels.

For this purpose, the invention proposes a process that consists in producing volatile fatty acids by anaerobic fermentation from various biomasses and in transforming these volatile fatty acids into hydrocarbons by electrolysis.

The production of hydrocarbons by electrolysis of volatile fatty acids has been known for more than 30 years. To this purpose, it is possible to cite, for example, the French patent FR2303854 and the U.S. Pat. No. 3,992,268. However, to date, this process has never been used industrially, because it operates with good mass and energy yields only with a high proportion (on the order of 90%) of acids having at least 5 to 6 carbon atoms (valeric acid and caproic acid) with primarily a high proportion (higher than 50%) of acids with more than 6 carbon atoms, whereas the anaerobic fermentation for the most part produces shorter-chain volatile fatty acids (caproic acid is in general only several percent and in the work conducted by LEVY, Liquid Fuels Production from Biomass, Dynatech 1980, this proportion, even after the addition of acetate, did not exceed 12%).

More recently, the possibility of elongation of volatile fatty acids by fermentation with a particular bacteria, *Clostridium kluyveri* (Matthew T. Agler et al.: Chain Elongation with Reactor Microbiomes: Upgrading Dilute Ethanol to Medium-Chain Carboxylates *Energy and Environmental Sciences* 2012), has been described. Nevertheless, this process requires the use of ethanol or hydrogen in large quantities, so it is not viable economically, the products that are obtained being too costly.

Furthermore, it is known that from common food sugars (glucose, sucrose), it is possible to obtain caproic acid, but taking into account the actual cost of the sugars of sacchariferous plants (on the order of 1,000 dollars per ton) and the final mass yield of the reactions (one ton of hydrocarbons per approximately 4 tons of sugar), it is completely improbable that it is possible to produce hydrocarbons economically from such sugars.

To remedy these drawbacks, this invention proposes a process comprising at least the following stages:
  a) Anaerobic fermentation of a fermentable raw material for obtaining volatile fatty acids,
  b) Elongation of the volatile fatty acids obtained in stage a) by fermentation with one or more bacteria of the genus *Megasphaera*, even more preferably with the bacterium *Megasphaera elsdenii*, and extraction of these acids from fermentation broth,
  c) Obtaining hydrocarbons by subjecting the fatty acids obtained in stage b) to Kolbe electrolysis.

Advantageously, the fermentation of sugars and volatile fatty acids by a bacterium of the genus *Megasphaera*, and in particular *Megasphaera elsdenii*, makes it possible to obtain for the most part fatty acids with a chain of at least 5 carbon atoms, without requiring the obligatory presence of ethanol or hydrogen.

The process is quite compatible with an industrial production, both in economic terms and thanks to its simplicity of implementation.

The hydrocarbons that are obtained can be used as automotive biofuels in a mixture with gasoline, diesel fuel, or kerosene, or as heating biofuels.

According to another advantage, the raw materials that can be used are numerous among the raw materials recommended for second-generation and third-generation biofuels.

DETAILED DESCRIPTION OF THE INVENTION

Other characteristics and advantages will emerge from the following detailed description of the invention.

The object of the invention is therefore a process for the production of hydrocarbons, comprising at least the implementation of the following stages:
  a) Anaerobic fermentation of a fermentable raw material for obtaining volatile fatty acids,
  b) Elongation of volatile fatty acids obtained in stage a) by fermentation with one or more bacteria of the genus *Megasphaera*, even more preferably with the bacterium *Megasphaera elsdenii*, and extraction of these acids from fermentation broth,
  c) Obtaining hydrocarbons by subjecting the fatty acids that are obtained in stage b) to Kolbe electrolysis.

The first stage consists in fermenting a biomass by anaerobic fermentation for obtaining volatile fatty acids.

Fermentable raw material or biomass is defined as any raw material that can produce volatile fatty acids by fermentation.

Preferably, the raw materials are selected among ligno-cellulosic plants as well as the waste and by-products of these plants, materials of animal origin, in particular meal and animal fatty substances, algae or by-products of algae, and waste and organic effluents.

The raw materials can be pretreated by an acid, a base, a solvent, a physical process, or enzymes before implementing stage a).

In a particularly suitable way, the raw materials without pretreatment or after pretreatment are selected from among:
The by-products (molasses, vinasse, sugar refinery waste, dregs) from sugar plants or starch plants, such as, for example, beets, sugar cane, or cereal grains,
The sugars that are obtained by hydrolysis of biomass of land-based origin (wood, short-rotation coppices, straw, stems), preferably preceded by a delignification, "whole-plant" harvested crops, such as, for example, corn or sorghum,
The sugars obtained by hydrolysis of biomass of aquatic origin, such as microalgae, macroalgae, or water hyacinths,
Effluents, or farming, agricultural, urban or industrial waste.

Advantageously, the microorganisms used for the anaerobic fermentation of the raw materials make it possible to ensure the first phase of hydrolysis of the cellulose and hemicelluloses by relying on simple pretreatments without necessarily having to use costly enzymes as is the case in numerous existing processes.

Stage a) is preferably carried out by pools of bacteria, as it is the case for fermentations that produce biogas or bacteria that produce short-chain volatile fatty acids (*Clostridium thermoaceticum, Tyrobutyricum*, or *Propionibacterium*, for example) alone or in a mixture. It can in particular be a matter of mesophilic fermentations (around 37° C.) or thermophilic fermentations (around 60-70° C.).

The volatile fatty acids that are obtained are for the most part short-chain acids: acetic, propionic and butyric.

Stage b) of the process according to the invention consists in elongating the carbon chain of these volatile fatty acids obtained in stage a) by fermentation with one or more bacteria of the genus *Megasphaera*, even more preferably with the bacterium *Megasphaera elsdenii*.

In terms of the invention, bacterium of the genus *Megasphaera* (or the bacterium *Megasphaera elsdenii*) is also defined as the recombinant bacteria incorporating genes of a bacterium of the genus *Megasphaera* (or the recombinant bacteria incorporating genes of the bacterium *Megasphaera elsdenii*).

The bacteria of the genus *Megasphaera* can be in particular wild bacteria obtained from rumen or ruminant effluents or waste from industrial processes such as those of beer-making, or bacteria obtained from the banks of microorganism strains. In addition to *Megasphaera elsdenii*, it is also possible to cite *Megasphaera cerevisae*.

Stage b) can be carried out under a cover of methane or with bubbling of methane.

The term "under a cover" of gas means that the gas is present above the liquid phase.

The term "with bubbling" of gas means that the gas is introduced in the form of bubbles into the liquid.

Stage b) can also be carried out:
Under a cover of biogas or with bubbling of biogas,
Under a cover of a mixture of methane, carbon dioxide and hydrogen or with bubbling of a mixture of methane, carbon dioxide, and hydrogen in variable proportions,
In the presence in the fermentation liquid of an additive inhibiting the co-enzyme M-reductase, such as 2-bromoethanesulfonate (BES) or any other inhibitor of the co-enzyme M-reductase that is known to one skilled in the art.

The cover or bubbling of gas or the presence of an inhibitor of the co-enzyme M-reductase makes it possible to improve the process by accelerating the speed of use of the sugars and short-chain fatty acids and by preventing the destruction of elongated fatty acids in the medium and their return to shorter-chain fatty acids.

Stage b) can also optionally be carried out in the presence of ethanol.

To result in a good effectiveness of the elongation process and to prevent the enzymes of the bacterium from destroying the medium-chain fatty acids that have been formed, stage b) is preferably to be carried out under specific conditions, in particular a pH between 5 and 6.5, and a very low oxidation-reduction potential, in particular between −500 mV and −600 mV.

The elongation stage b) with *Megasphaera* is essential and is to make it possible before extraction to obtain fatty acids of which at least 40% are fatty acids with a chain of 6 carbon atoms.

Very preferably, stages a) and b) are carried out separately.

According to a first variant, stages a) and b) can be carried out together in one stage by co-cultivating, in a single fermenter, the fermentable raw material with a microorganism that is capable of hydrolyzing cellulose and one or more bacteria of the genus *Megasphaera*, even more preferably with the bacterium *Megasphaera elsdenii*.

According to a second variant, the stages a) and b) are carried out together with pools of bacteria to which is added an inoculum based on a bacterium of the genus *Megasphaera*, even more preferably with the bacterium *Megasphaera elsdenii*.

Once the elongation is carried out, the elongated volatile fatty acids should preferably be extracted from the fermentation broth to implement stage c).

The short-chain fatty acids (primarily acetic and butyric acids) remaining in the fermentation broth in stage b) after extraction of elongated fatty acids can be reused in stages a) or b) or else used for producing alkenes by the Hofer-Moest variant of Kolbe electrolysis.

In a preferred way, extraction is done in a continuous manner, outside of the fermenter or inside the fermenter if it is a matter of a two-phase fermenter, with the aqueous and organic phases being simply superposed or subjected to actions making it possible to reinforce their interface (stirring, bubbling, etc.).

According to a particularly suitable embodiment, this extraction can be done with an extractant and/or a solvent. The extractant can be selected, for example, from among the organophosphorus compounds such as trioctylphosphine oxide and the tertiary or quaternary fatty amines such as trioctylamine. The solvent can be selected, for example, from among alcohols, esters, alkanes, and mixtures of hydrocarbons, such as kerosene. Preferably, the extractant and the solvent are used inside the fermenter in a two-phase fermentation.

According to another variant, this extraction can be carried out with a membrane contactor, which makes it possible to avoid putting the extractant and the solvent into contact with the bacterium.

This extraction method can preferably be implemented in aqueous medium with a water-repellent membrane that, surprisingly, very preferably extracts the acids with 6 carbon atoms and more, which makes it possible to increase the concentration of such acids.

Stage b) after extraction leads to a mixture of fatty acids comprising more than 50% acids with 6 carbon atoms and more than 90% acids with 5 carbon atoms and more, which corresponds to the conditions that are necessary for making the Kolbe electrolysis economical, with the other fatty acids able to be recycled in the anaerobic fermentation stage a).

Stage c) then consists in subjecting the fatty acids that are obtained in stage b) to electrolysis. This electrolysis is known under the name of Kolbe electrolysis.

At the anode, the reaction is an oxidation that leads to the formation of the acid radical $RCOO^{500}$. Then, two radicals of this type combine to "dimerize," which results in the formation of $CO_2$ and a hydrocarbon R—R with a chain length that is double that of the original molecule minus one carbon atom. At the cathode, the H+ ions lead to the formation of hydrogen that escapes in the form of $H_2$ gas.

There are different variants of this electrolysis, one of which consists in making a dimerization crossed between a volatile fatty acid and vegetable oil fatty acids.

This electrolysis from volatile fatty acids obtained according to the invention in stage b) makes it possible to obtain hydrocarbons.

Preferably, the hydrocarbons that are obtained are alkanes with a chain of at least 8 carbon atoms, even more preferably alkanes with a chain of 8 to 14 carbon atoms.

Stage c) can be followed by a stage d) for purification of the hydrocarbons that are obtained, according to any known chemical or physical process, such as, for example, washing with water, cleaning by a solvent, distillation, etc.

These hydrocarbons can be used as automotive biofuels in a mixture with gasoline, with kerosene, or with diesel fuel, or else as heating biofuels.

In stage c), an accompanying reaction can take place at the anode with the short-chain volatile fatty acids that are present at the same time as the acids with 5 or 6 carbon atoms, which preferably leads to the formation of alkenes such as ethylene and propylene. These products can serve as a basis for the production of numerous chemical products including polymers such as polyethylene and polypropylene.

According to an embodiment, the process according to the invention can also comprise stages making it possible to upgrade the co-products.

The invention is now illustrated by an example for conducting tests and by the results of such tests.

Stages a) and b)

Example 1

A fermentation test of a solution with 4% saccharose in water with the strain NCIMB 702410 of *Megasphaera elsdenii* was carried out in the course of 7 days at 37° C. in a 500 ml Erlenmeyer flask containing:

250 ml of biological medium (based on known nutritional elements: yeast extract, peptones, meat extract) with saccharose as an additive or other sugars and 5 g/l of sodium butyrate, 2 ml aliquot of the bacterial strain, 100 ml of extraction solvent (Alamine 336 at 10% in an oleic alcohol solution), and Above, a methane cover (>99%) in a sterile medium.

After 7 days, the production of the volatile fatty acids was metered by gas phase chromatography. The composition of aqueous phases and organic phases obtained is presented in Table 1 below:

TABLE 1

|  | Aqueous Phase | Organic Phase | Total in the 2 Phases in g/l | Acid Profile for the 2 Phases |
|---|---|---|---|---|
| Formic Acid | 0.0 | 0.3 | 0.3 | 1.2% |
| Acetic Acid | 0.3 | 0.3 | 0.6 | 2.2% |
| Propionic Acid | 0.0 | 0.0 | 0.0 | 0.2% |
| Isobutyric Acid | 0.2 | 0.4 | 0.6 | 2.3% |
| Butyric Acid | 2.9 | 2.6 | 5.5 | 22.1% |
| Isovaleric Acid | 0.4 | 1.1 | 1.5 | 5.9% |
| Valeric Acid | 1.4 | 4.7 | 6.1 | 24.2% |
| Caproic Acid | 0.8 | 9.8 | 10.6 | 41.9% |

The total proportion of caproic acid is 42%, and the proportion in the organic phase is 51%. The total proportion of acids with 5 carbon atoms and more (valeric, isovaleric, and caproic acids) in the two phases is 72%. The proportion in the organic phase is 81%.

Example 2

The same test was carried out with glucose instead of saccharose. The total proportion of acids with 5 carbon atoms and more in the two phases is greater than 73%, and the proportion in the organic phase is more than 90%.

Example 3

A fermentation test of an aqueous solution initially comprising 7.6 g/l of acetic acid and 5.2 g of glucose with the strain NCIMB 702410 of *Megasphaera elsdenii* was carried out at 37° C. with a pH regulated at 6 and a redox potential of less than 500 mV, in a bioreactor with a useful volume of 2.5 liters equipped with a membrane contactor for extraction/concentration of fatty acids. Glucose was added regularly when the concentration dropped below 0.2 g/l.

At the end of 112 hours, the total quantity of fatty acids in the reactor and the extractor was in total 14.2 g/l, including 7.4 g/l of butyric acid, 0.2 g/l of valeric acid, and 6.4 g/l of caproic acid (45%). The concentration of acetic acid was brought from 7.6 to 2.2 g/l that is a consumption of 5.4 g/l, and the consumption of glucose was 17.5 g/l.

It therefore appears that a significant production of caproic acid was obtained, of which the carbon came in part from glucose and in part from acetic acid. Since a portion of the acetic acid has also been transformed into butyric acid, it is possible to affirm that a true elongation of the acetic acid into butyric and caproic acids was initiated. The overall mass yield was 56%, and the productivity of caproic acid reached 0.10 g/l/h at the end of the fermentation.

Example 4

It involves a test similar to the preceding one. At the end of 140 hours, 20 g/l of glucose and 6.4 g/l of acetate were consumed, and 8.5 g/l of caproic acid and 8.2 g/l of butyric acid were produced. There was therefore an elongation of acetic acid into butyric acid and caproic acid, and the overall mass yield was 63%.

The extraction by ion exchange resins, which was done after the test, very preferably focused on the caproic acid, since the proportion of caproic acid obtained after recovery on the resins was 96%. The thus obtained acids can be easily used for electrolysis since they are not in aqueous solution.

This test shows that it is possible to extract an acid solution that is very concentrated in caproic acid, able to provide high alkane yields by Kolbe electrolysis, with the acids that have not been extracted (for the most part acetic and butyric acids) being able to be recycled in the fermenter for a new elongation by *Megasphaera* or else recovered to produce alkenes by the Hofer-Moest variant of the Kolbe electrolysis.

Example 5

This last test made it possible to implement the stages a) and b) successively. 300 g (raw) of potato peels in 2,700 ml of water was subjected to an anaerobic fermentation with 300 ml of inoculum (manure digester/dry straw). The fermenter was regulated at 55° C. as well as at pH 5.8. The methanogenesis was inhibited by 0.1340 g of BES (2-bromoethane sulfonate). At the end of 400 hours, the concentrations of short-chain volatile fatty acids obtained in the first stage or present at the beginning of the fermentation were 2.2 g/l of acetic acid, 0.7 g/l of propionic acid, and 1 g/l of butyric acid.

The fermentation broth after filtration was subjected to fermentation by *Megasphaera* by adding to the residue of the preceding fermentation after draw-off. At the beginning of the fermentation, the concentrations were 3 g/l of acetic acid, 3.5 g/l of butyric acid, 0.2 g/l of valeric acid, and 2.4 g/l of caproic acid. At the end of 120 hours, the total recovered quantity of fatty acids, brought back to the volume of the fermenter and extractor, was 18 g/l, including 1.2 g/l of acetic acid, 8 g/l of butyric acid, 0.8 g/l of valeric acid, and 8 g/l of caproic acid. The consumption of glucose was 19.5 g/l, and that of acetic acid was 1.8 g/l. An elongation of the short-chain acids initially present or obtained in stage a) was again obtained, primarily toward butyric acid and caproic acid, with an overall mass yield of 18 g/l on 19.5 g/l of glucose plus 9.1 g/l of volatile fatty acids, present at the beginning or 63%.

The elution from resins made it possible to extract a mixture that comprises 81% of caproic acid. This composition that was obtained is therefore very advantageous for implementing Kolbe electrolysis.

Stage c)

Example 6

A filter-press-type electrolysis cell was assembled. It consists of two graphite plates designed for allowing the reactive solution to access the electrodes. Two platinum electrodes (25 cm$^3$) were placed on each graphite plate.

80 ml of a caproic acid solution with 1 mol·L-1 in NaOH was placed in a graduated tube having an outlet and an inlet, and then subjected to electrolysis. This device makes it possible to measure the quantities of solution to be added to keep the concentration at a constant level, while measuring the voltage and the intensity of the current and the quantity of products obtained that float to the top of the solution.

The detected products are the following:
90% of decane,
9% of pentyl caproate, and
Several products obtained from impurities that are present in the reagents that are used.

The overall mass yield is almost 100% of the theoretical yield, and the electrical consumption was 1.75 kWh/liter of product, which represents approximately 15% of the energy value of the fuel obtained.

Example 7

The same test was carried out with a solution comprising 75% caproic acid and 25% valeric acid. The detected products were almost only alkanes with 8 carbon atoms. The electrical consumption was 2.5 kWh/liter of product, which represents approximately 22% of the energy value of the fuel obtained.

Example 8

The same test was carried out with a solution comprising 50% caproic acid, 20% valeric acid, 20% isovaleric acid, 10% butyric acid (synthetic broth that is representative of the broth that is currently obtained in a fermentation by *Megasphaera*). The products obtained were at most 90% alkanes with 8 carbon atoms and more (octane, nonane, decane). The electrical consumption was 2.1 kWh/liter of product, which represents approximately 18% of the energy value of the fuel obtained.

Example 9

The same test was carried out with a solution comprising 70% caproic acid, 20% valeric acid, 5% isovaleric acid, and 5% butyric acid (synthetic broth). The products that were obtained were almost only alkanes with 8 carbon atoms and more: octane 6%, nonane and methyl-octane 29%, decane 65%. The electrical consumption was 1.7 kWh/liter of product, which represents approximately 15% of the energy value of the fuel obtained.

In an unexpected manner relative to the state of the art, these tests show that the process according to the invention makes it possible to obtain a very high proportion of alkanes that have 8 carbon atoms and that are most usable as automotive fuels in a mixture in gasoline, kerosene, or diesel fuel or as heating biofuels. The process is also relatively simple, with high mass yields (approximately 5 tons of dry biomass are necessary per one ton of hydrocarbons, which is only just below the theoretical yield) and low electrical energy consumption, thus making possible an economically viable and very advantageous operation.

The invention claimed is:
1. A process for producing hydrocarbons, comprising at least the implementation of the following stages:
   a) conducting anaerobic fermentation of a fermentable raw material for obtaining volatile fatty acids,
   b) elongating the volatile fatty acids obtained in stage a) by carrying out fermentation of the volatile fatty acids with one or more bacteria of *Megasphaera elsdenii* at a redox potential between −500 and −600 mV, obtaining a fermentation broth, and extracting fatty acids obtained from the fermentation broth, and
   c) obtaining hydrocarbons by subjecting the fatty acids obtained in stage b) to Kolbe electrolysis.
2. The process for producing hydrocarbons according to claim 1, wherein stage b) is carried out with a pH between 5.5 and 6.5.
3. The process for producing hydrocarbons according to claim 1, wherein stage b) for fermentation of volatile fatty acids with *Megasphaera elsdenii* is carried out under conditions selected from the group consisting of under a cover of methane or with bubbling of methane, under a cover of biogas or with bubbling of biogas, under a cover of a mixture of methane, carbon dioxide, and hydrogen or with bubbling of a mixture of methane, carbon dioxide, and hydrogen in variable proportions, and in the presence of an additive inhibiting the co-enzyme M-reductase in fermentation liquid.

4. The process for producing hydrocarbons according to claim 1, wherein stage b) is carried out in the presence of ethanol.

5. The process for producing hydrocarbons according to claim 1, wherein the fatty acids that are obtained in stage b) comprise fatty acids with a chain of at least 5 carbon atoms.

6. The process for producing hydrocarbons according to claim 1, wherein the fatty acids that are obtained in stage b) comprise fatty acids with a chain of 6 to 8 carbon atoms.

7. The process for producing hydrocarbons according to claim 1, wherein the fatty acids that are obtained in stage b) are:
at least 50% of fatty acids containing 6 carbon atoms, and
at least 90% of fatty acids containing 5 carbon atoms.

8. The process for producing hydrocarbons according to claim 1, wherein the hydrocarbons that are obtained in stage c) comprise alkanes with a chain of at least 8 carbon atoms.

9. The process for producing hydrocarbons according to claim 1, wherein the hydrocarbons that are obtained in stage c) comprise alkanes with a chain of 8 to 14 carbon atoms.

10. The process for producing hydrocarbons according to claim 1, wherein stages a) and b) are carried out together in only one stage.

11. The process for producing hydrocarbons according to claim 10, wherein stages a) and b) are carried out together by co-cultivating the fermentable raw material with a microorganism that is capable of hydrolyzing cellulose and *Megasphaera elsdenii*.

12. The process for producing hydrocarbons according to claim 10, wherein stages a) and b) are carried out together with bacteria pools reinforced with *Megasphaera elsdenii*.

13. The process for producing hydrocarbons according to claim 1, wherein the elongated volatile fatty acids that are obtained in stage b) are extracted from the fermentation broth in a continuous manner.

14. The process for producing hydrocarbons according to claim 1, wherein in stage b) after extraction of the elongated fatty acids, short-chain fatty acids remaining in the fermentation broth are reused in stages a) or b) or to produce alkenes by the Hofer-Moest variant of Kolbe electrolysis.

15. The process for producing hydrocarbons according to claim 1, wherein the elongated volatile fatty acids that are obtained in stage b) are extracted from the fermentation broth with an extractant and/or a solvent.

16. The process for producing hydrocarbons according to claim 15, wherein the extractant is selected from the group consisting of organophosphorus compounds and tertiary or quaternary fatty amines, and the solvent is selected from the group consisting of alcohols, esters, alkanes, and hydrocarbon mixtures.

17. The process for producing hydrocarbons according to claim 15, wherein the extractant and the solvent are used inside a two-phase fermenter.

18. The process for producing hydrocarbons according to claim 1, wherein the elongated volatile fatty acids that are obtained in stage b) are extracted with a membrane contactor with a water-repellent membrane.

19. The process for producing hydrocarbons according to claim 1, further comprising a stage d) for purification of the hydrocarbons that are obtained in stage c).

20. The process for producing hydrocarbons according to claim 1, wherein the fermentable raw materials are pretreated before stage a) by an acid, a base, a solvent, a physical process, or enzymes.

21. The process for producing hydrocarbons according to claim 1, wherein the fermentable raw materials are selected from the group consisting of by-products of sugar plants or starch plants, sugars that are obtained by hydrolysis of biomass of land-based origin optionally preceded by a delignification, and sugars obtained by hydrolysis of biomass of aquatic origin, effluents, or farming, agricultural, urban or industrial waste.

* * * * *